US011590338B2

(12) United States Patent
Barry

(10) Patent No.: US 11,590,338 B2
(45) Date of Patent: Feb. 28, 2023

(54) HEART PUMP WITH PASSIVE PURGE SYSTEM

(71) Applicant: ABIOMED, Inc., Danvers, MA (US)

(72) Inventor: Vincent Barry, Danvers, MA (US)

(73) Assignee: ABIOMED, INC., Danvers, MA (US)

(*) Notice: Subject to any disclaimer, the term of this patent is extended or adjusted under 35 U.S.C. 154(b) by 0 days.

(21) Appl. No.: 17/526,658

(22) Filed: Nov. 15, 2021

(65) Prior Publication Data

US 2022/0152377 A1     May 19, 2022

Related U.S. Application Data

(63) Continuation of application No. 15/845,947, filed on Dec. 18, 2017, now Pat. No. 11,202,901.

(Continued)

(51) Int. Cl.
*A61M 60/829*     (2021.01)
*A61M 60/148*     (2021.01)
*A61M 60/824*     (2021.01)
*A61M 60/13*      (2021.01)
*A61M 60/414*     (2021.01)
(Continued)

(52) U.S. Cl.
CPC .......... *A61M 60/829* (2021.01); *A61M 60/13* (2021.01); *A61M 60/148* (2021.01);
(Continued)

(58) Field of Classification Search
CPC .............. A61M 60/829; A61M 60/824; A61M 60/148; A61M 60/135; A61M 60/50;
(Continued)

(56) References Cited

U.S. PATENT DOCUMENTS

| 6,244,835 B1* | 6/2001 | Antaki | F04D 13/0646 417/423.1 |
| 2003/0100816 A1* | 5/2003 | Siess | A61M 60/531 600/16 |

(Continued)

FOREIGN PATENT DOCUMENTS

| EP | 0364293 A2 | 4/1990 |
| EP | 0629412 A2 | 12/1994 |

(Continued)

OTHER PUBLICATIONS

Office Action from corresponding Australian Application No. 2017378806 dated Jun. 29, 2022 (3 pages).

(Continued)

*Primary Examiner* — Tammie K Marlen
(74) *Attorney, Agent, or Firm* — Botos Churchill IP Law LLP

(57) ABSTRACT

A heart pump assembly includes an elongate catheter with a proximal portion and a distal portion, a rotor at the distal portion of the elongate catheter, a driveshaft, and a bearing. The rotor can include an impeller blade shaped to induce fluid flow in a first axial direction. The drive shaft may be coupled to or integrally formed with a proximal end of the rotor and can include a pump element formed in a surface of the drive shaft. The bearing can include a bore into which the drive shaft extends. The pump element is shaped so as to induce fluid flow through the bore in a second axial direction which can be the same or opposite to the first axial direction.

20 Claims, 8 Drawing Sheets

Related U.S. Application Data

(60) Provisional application No. 62/436,016, filed on Dec. 19, 2016.

(51) Int. Cl.
*A61M 60/237* (2021.01)
*A61M 60/585* (2021.01)
*A61M 60/538* (2021.01)
*A61M 60/825* (2021.01)

(52) U.S. Cl.
CPC ........ *A61M 60/237* (2021.01); *A61M 60/414* (2021.01); *A61M 60/538* (2021.01); *A61M 60/585* (2021.01); *A61M 60/824* (2021.01); *A61M 60/825* (2021.01)

(58) Field of Classification Search
CPC .. A61M 60/585; A61M 60/00; A61M 60/237; A61M 60/205; A61M 60/818; A61M 60/538; A61M 60/414; A61M 60/13; A61M 60/825; A61M 1/102; A61M 1/1017; A61M 1/122; A61M 1/125; A61M 1/1086; A61M 1/101; A61M 1/1031; A61M 1/12
See application file for complete search history.

(56) References Cited

U.S. PATENT DOCUMENTS

| | | |
|---|---|---|
| 2012/0101455 A1 | 4/2012 | Liebing |
| 2015/0051436 A1 | 2/2015 | Spanier et al. |
| 2016/0303299 A1 | 10/2016 | Muller |

FOREIGN PATENT DOCUMENTS

| | | |
|---|---|---|
| EP | 1352980 A1 | 10/2003 |
| JP | S61500058 A | 1/1986 |
| JP | H06346917 A | 12/1994 |
| JP | 4176471 B2 | 8/2008 |
| JP | 2015508678 A | 3/2015 |
| WO | 8501436 A1 | 4/1985 |
| WO | 2010124882 A1 | 11/2010 |
| WO | 2016116608 A2 | 7/2016 |

OTHER PUBLICATIONS

International Preliminary Report on Patentability for corresponding International Application No. PCT/US2017/066967 dated Jun. 25, 2019 (8 pages).
Written Opinion from corresponding Singapore Application No. 11201905534U dated Oct. 26, 2020 (7 pages).
International Search Report for corresponding International Application No. PCT/US2017/066967, dated Mar. 4, 2018 (6 pages).
Office Action for corresponding Chinese Application No. 201790001609.8 dated Jun. 10, 2020 (3 pages).
Office Action from corresponding Indian Patent Application No. 201917026181 dated Dec. 14, 2021 (7 pages).
Office Action from corresponding Japanese Patent Application No. 2019-533042 dated Dec. 1, 2021 (9 pages).
Decision to Grant issued in corresponding JP Patent Application No. 2019-533042 dated Jul. 20, 2022 (6 pp.).
Office Action for corresponding SG Application No. 11201905534U dated Jul. 6, 2022 (5 pages).

* cited by examiner

HEART PUMP WITH PASSIVE PURGE SYSTEM

CROSS-REFERENCE TO RELATED APPLICATIONS

The present application is a continuation of U.S. patent application Ser. No. 15/845,947, filed Dec. 18, 2017, issued as U.S. Pat. No. 11,202,901 on Dec. 21, 2021, which claims priority to U.S. Provisional Patent Application No. 62/436,016, filed Dec. 19, 2016, the entire disclosures of which are hereby incorporated herein by reference.

BACKGROUND

Heart pumps, such as percutaneous intracardiac heart pump assemblies, can be introduced into the heart to deliver blood from the heart into an artery. When deployed in the heart, heart pump assemblies can pull blood from the left ventricle of the heart and expel blood into the aorta, or pull blood from the right ventricle and expel blood into the pulmonary artery. Heart pump assemblies can be introduced surgically or percutaneously during cardiac procedures. In one common approach, pump assemblies can be inserted by a catheterization procedure through the femoral artery.

A heart pump may include a rotor which rotates on a rotor shaft to draw blood through the pump. The rotor shaft may rotate within a bore of a bearing included in the heart pump. The space between the rotor shaft and the bore of the bearing can define a rotor-bearing cavity. As the rotation of the rotor pulls blood toward or away from the pump (depending on whether the pump is designed for use in the left or right side of the patient's heart), blood may enter the pump through the rotor-bearing cavity, potentially stopping the pump.

To prevent blood ingress into the pump, purge fluid may be flowed into the pump from an external source through a purge line. A continuous flow of hemocompatible fluid may be pumped through the pump and through the rotor-bearing cavity to prevent blood from entering the pump at the rotor-bearing cavity. Commercially available purge systems require a dedicated external pump to pressurize and deliver the hemocompatible fluid to the rotor-bearing cavity. The external pump controlling the purge fluid flow may be bulky for a healthcare setting where space is limited (e.g., an operating room or catheterization lab). Furthermore, operation of an external purge pump in addition to the controller for the heart pump may be inconvenient or unintuitive for health care professionals. External purge pumps are large and inconvenient for ambulation/portable use.

SUMMARY

Systems, methods, and devices are described herein for a heart pump having a rotor assembly which induces simultaneous flow of a first fluid and a second fluid by a single rotor assembly. Such a system can provide a first pressure gradient to pump a first fluid (e.g., blood) in a first direction (e.g., from the left ventricle into the aorta or from the inferior vena cava to the pulmonary artery) and a second pressure gradient to pump a second fluid (e.g., purge fluid, lubricant, coolant, medicine, or any suitable hemocompatible fluid) in a second direction (e.g., along the rotor shaft and into the left ventricle). Since the flow of purge fluid can be induced by the same mechanism as the flow of blood, the rotor assembly is said to be a "passive purge system." A passive purge system can eliminate or reduce the need for an external pressurizing pump since the purge fluid can be pumped by the same rotor that pumps the blood. Eliminating or shrinking the purge system's external pump can reduce the amount of space occupied by the controller for the overall pump system in a healthcare environment, and for ambulation and at home care. In the context of out-patient care, eliminating the additional pump for the purge system may increase patient mobility because it may enable full implantation of the pump. Furthermore, flow of the second fluid can provide a barrier against blood ingress into sensitive regions of the pump (e.g., the bore in which the rotor shaft rotates). These effects can allow the pump to be used on a long-term basis without additional equipment.

The second pressure gradient can be induced by a pump element formed on the drive shaft of the rotor assembly. The pump element can be formed on a surface of the rotor drive shaft such that the rotation of the drive shaft during operation of the pump generates the second pressure gradient. For example, the pump elements can be formed as blades, grooves, scratches, and/or etches on the rotor drive shaft surface. In some implementations, the rotor drive shaft extends into or through a bore. When the rotor drive shaft rotates within the bore, the second fluid can be drawn from an external reservoir and through the bore. In certain implementations, the pump elements are formed on the outer surface of the bore in addition to or instead of being formed on the outer surface of the rotor drive shaft.

In some implementations, the rotor assembly is driven by an implantable motor having a motor rotor and motor stator. The second pressure gradient induced by the rotor can flow the second fluid (e.g., purge fluid, lubricant, coolant, medicine, or any suitable hemocompatible fluid) through the gap between the motor rotor and the motor stator and along the drive shaft. The flow of the second fluid can provide a barrier against blood ingress into the gap between the motor rotor and the motor stator which could otherwise cause damage to the blood (e.g., hemolysis) or damage to the motor (e.g., increased friction, overheating, and/or seizing).

In one aspect, a heart pump assembly includes an elongate catheter with a proximal portion and a distal portion, a rotor at the distal portion of the elongate catheter, a driveshaft and a bearing. The rotor further includes an impeller blade shaped to induce fluid flow in a first axial direction. The drive shaft may be coupled to a proximal end of the rotor and includes a pump element formed on a surface of the drive shaft. The bearing includes a bore into which the drive shaft extends. The pump element is shaped to induce fluid flow through the bore in a second axial direction.

In some implementations, the second axial direction is opposite to the first axial direction. In other implementations, the second axial direction is substantially the same as the first axial direction. In some implementations, the heart pump assembly includes a fluid supply line in fluid communication with the bore of the bearing and the pump element is able to draw fluid from the fluid supply line through the bore. In some implementations, the pump element is located in a bearing gap between the drive shaft and a sleeve bearing. In some implementations, the bearing gap between the drive shaft and the sleeve bearing is in the range of about 5-10 microns. In some implementations, the pump element is shaped as a groove on the surface of the drive shaft. In some implementations, the groove on the surface of the drive shaft is angled with respect to a longitudinal axis of the drive shaft. In some implementations, the pump element is shaped as a protrusion on the surface of the drive shaft.

In some implementations, a ratio of the flow rate of the fluid flow in the second axial direction to a flow rate of the fluid flow in a first axial direction is about 0.001-0.03%. In some implementations, the flow rate of the fluid flow in the first axial direction is about 2-5 liters per minute (lpm). In some implementations, the flow rate of the fluid flow in the second axial direction is about 2-30 cc/hr.

In some implementations, the drive shaft is coupled to a motor. In some implementations, the heart pump further includes a pump housing enclosing the rotor and bearing. In some implementations, the pump housing is sized for percutaneous insertion. The heart pump assembly may also include a blood outlet positioned proximal to a proximal end of the pump housing and a blood inlet positioned at a distal end portion of a cannula of the pump assembly. In other implementations, the heart pump assembly may also include a blood outlet positioned at a distal end portion of a cannula of the pump assembly, and a blood inlet positioned proximal to a proximal end of the pump housing.

In another aspect, a heart pump assembly includes an elongate catheter having a proximal portion and a distal portion, a rotor, a drive shaft and a bearing. The rotor is disposed at the distal portion of the elongate catheter and includes an impeller blade shaped to induce fluid flow in a first axial direction. The drive shaft is coupled to a proximal end of the rotor. The bearing includes a bore into which the drive shaft extends and includes a pump element formed in a surface of the bore. The pump element is shaped to induce fluid flow through the bore in a second axial direction. In some implementations, the first axial direction is opposite to the second axial direction. In other implementations, the first axial direction and the second axial direction are substantially the same.

In some implementations, the pump element is shaped as a groove on the surface of the bore. In some implementations, the groove on the surface of the bore is angled with respect to a longitudinal axis of the drive shaft. In other implementations, the pump element is shaped as a protrusion on the surface of the bore. In some implementations, the ratio of the flow rate of the fluid flow in the second axial direction to a flow rate of the fluid in a first axial direction is about 0.001-0.03%. In some implementations, the flow rate of the fluid flow in the first axial direction is about 2-5 lpm. In some implementations, the flow rate of the fluid flow in the second axial direction is about 2-30 cc/hr.

In another aspect, a method for providing cardiac assistance includes positioning a heart pump in a patient's vasculature, wherein the heart pump comprises a rotor assembly having a first pump element and a second pump element wherein the first and second pump elements rotate together. The method further includes rotating the rotor assembly to induce a blood flow in a first axial direction with the first pump element while concurrently inducing fluid flow in a second axial direction with the second pump element. The rate of fluid flow induced by the second pump element is less than 1% of the rate of blood flow.

In some implementations, the second axial direction is opposite to the first axial direction. In some implementations, the second axial direction is substantially the same as the first axial direction. In some implementations, the fluid flow induced by the second pump element is drawn through a fluid supply line. In some implementations, the fluid flow induced by the second pump element is through a bearing gap. In some implementations, the bearing gap is about 5 microns or less. In some implementations, the blood flow in the first axial direction surrounds the fluid flow in the second axial direction. In some implementations, a ratio of a flow rate of the fluid flow in the second direction to flow rate of the fluid flow in the first axial direction is about 0.001-0.03%. In some implementations, the flow rate of the fluid flow in the first axial direction is about 2-5 lpm. In some implementations, the flow rate of the fluid flow in the second axial direction is about 2-30 cc/hr.

In some implementations, the second pump element is shaped as a groove on a surface of the rotor assembly. In other implementations, the second pump element is shaped as a protrusion on a surface of the rotor assembly. In some implementations, the step of positioning a heart pump in a patient's vasculature includes percutaneous implantation of the pump into the heart.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
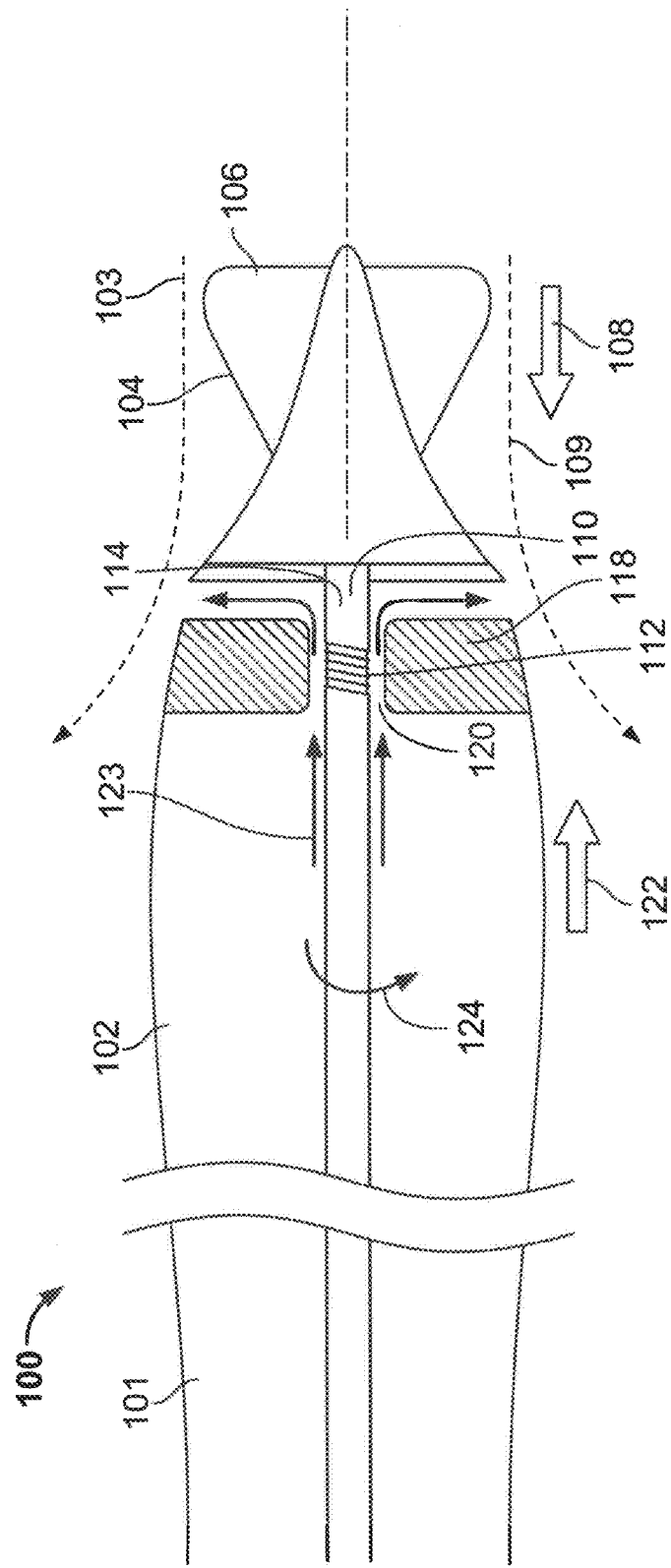
FIG. 1 shows a lateral section view of an illustrative drive shaft of a heart pump having pump elements on the rotor drive shaft for pumping a purge fluid.

To provide an overall understanding of the systems, method, and devices described herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of cardiac therapy and cardiac assist devices, including cardiac assist devices implanted using a surgical incision, and the like. Additionally, though the application of pump elements has been described here with regard to heart pumps, it is to be understood that the pump elements may be applied to other pumps for which fluid flow of a purging, lubricating, and/or cooling fluid is required. For example, pumps which are used in acidic or otherwise corrosive environments may require a purge flow to prevent the ingress of acid which would be damaging to pump components.

Systems, methods, and devices are described herein for a heart pump having a rotor assembly which induces simultaneous fluid flow. Such a system can provide a first pressure gradient to pump a first fluid (e.g., blood) in a first direction (e.g., from the left ventricle and into the aorta) and a second pressure gradient to pump a second fluid (e.g., purge fluid, lubricant, coolant, medicine, or any suitable hemocompatible fluid) in a second direction (e.g., along the rotor shaft and into the left ventricle) which can be the same or different from the first direction. Since the two pressure gradients are both generated by the rotation of the same rotor assembly, the second pressure gradient may be considered dependent or parasitic on the first pressure gradient. Thus, when the second pressure gradient is used to pump a purge fluid, the purge system may be said to be a "passive purge mechanism." A passive purge mechanism can eliminate or reduce the need for an external pressurizing pump since the purge fluid can be pumped by the same rotor that pumps the blood. Eliminating or shrinking the purge system's external pump can reduce the amount of space occupied by the controller for the overall pump system in a healthcare environment. Additionally, elimination of a dedicated pump for the purge system can simplify the workflow for the system operator. In out-patient use as a fully implantable pump configured for long term implantation, the elimination of the additional pump for the purge system may increase patient mobility. Furthermore, flow of the second fluid can provide a barrier against blood ingress into sensitive regions of the pump (e.g., the bore in which the rotor shaft rotates). These effects can allow the pump to be used on a long-term basis without additional equipment.

The second pressure gradient can be induced by a pump element formed on the drive shaft of the rotor assembly. The pump element can be formed on a surface of the rotor drive shaft such that the rotation of the drive shaft during operation of the pump generates the second pressure gradient. For example, the pump elements can be formed as blades, grooves, scratches, and/or etches on the rotor drive shaft surface. In some implementations, the rotor drive shaft extends into or through a bore. When the rotor drive shaft rotates within the bore, the hemocompatible fluid can be drawn from an external reservoir and through the bore. In certain implementations, the pump elements are formed on the outer surface of the bore in addition to or instead of being formed on the outer surface of the rotor drive shaft.

In some implementations, the rotor assembly is driven by a rotor and motor stator. The second gradient induced by the rotor can flow the second fluid (e.g., purge fluid, lubricant, coolant, medicine, or any suitable hemocompatible fluid) through the gap between the rotor and bearing. The flow of the second fluid can provide a barrier against blood ingress into the rotor-bearing gap which could otherwise damage to the pump (e.g., due to fluid entering the motor, increased friction, overheating, and/or seizing).

FIG. 1 shows a lateral section view of an illustrative drive shaft of a heart pump 100 having pump elements 112 on the rotor drive shaft 110 according to some implementations. The heart pump 100 includes an elongate catheter 105 having a proximal portion 101 and a distal portion 103, a rotor 104, an impeller blade 106, a drive shaft 110, a drive shaft surface 114, a pump element 112, a distal bearing 118, and a bore 120. The rotor 104 is located at the distal portion 103 of the elongate catheter 105. The rotor 104 is rotated in a direction 124 by the drive shaft 110 which extends through the bore 120. The rotor 104 includes an impeller blade 106 shaped to induce a fluid flow 109 in a first axial direction 108. The pump element 112 is formed on the surface 114 of the drive shaft 110 and is shaped to induce a flow of a second fluid 123 through the bore 120 in a second direction 122 during rotation of the drive shaft 110. As shown in FIG. 1, the second direction 122 is opposite the first axial direction 108. In some implementations, the first axial direction 108 and the second direction 122 may have different relative orientations. For example, the second direction 122 may be skew, perpendicular, or parallel to the first axial direction 108. In some implementations, the first axial direction 108 and the second direction 122 may be the same. In other embodiments, the motor need not be implantable in a patient's body. For example, the motor may be positioned outside of a patient's body and the rotor drive shaft can extend from the motor and drive the pump.

The pump element 112 may be formed on the drive shaft 110 as a groove, scratch, microvein, protrusion, or any other suitable feature. Addition of a groove or scratch to the drive shaft 110 during manufacture requires only material removal and can be easily added to the manufacture process. A groove on the surface of the drive shaft 110 is less likely to damage the bore 120 in which the shaft rotates if the rotation includes eccentricities. The pump element 112 may be formed on the surface 114 of the drive shaft 110 at an angle relative to a longitudinal axis of the drive shaft 110. The pump element 112 may be formed at an angle of 5.degree., 10.degree., 15.degree., 20.degree., 25.degree., 30.degree., or any other suitable angle relative to a longitudinal axis of the drive shaft 110. In some implementations, the pump element 112 is formed as a continuous groove, scratch or protrusion from the surface 114 of the drive shaft 110 which winds around the surface 114 of the drive shaft 110. In certain implementations, the pump element 112 may be formed as a series of distinct elements disposed circumferentially around the surface 114 of the drive shaft 110. In some implementations, the pump element 112 is formed on the surface 114 of the drive shaft 110 only at a portion of the drive shaft 110 which extends through the bore 120 of the distal bearing 118. In some implementations, the pump element 112 extends onto a portion of the drive shaft 110 which is proximal to the section of the drive shaft 110 which extends through the bore 120 of the distal bearing 118.

During operation of the heart pump 100, the drive shaft 110 rotates the impeller blade 106 in the direction 124. The rotation of the impeller blade 106 induces a first pressure gradient causing a first fluid flow 109 (e.g., a flow of blood) in the first axial direction 108. As shown, the first axial direction 108 of fluid flow 109 points from the distal portion 103 of the elongate catheter 105 toward the proximal portion 101 of the elongate catheter 105. Blood may flow in the first axial direction 108 when blood is pumped from a patient's left ventricle into the patient's aorta to increase cardiac output. While the impeller blade 106 rotates, the pump element 112 also rotates in the direction 124. The rotation of the pump element 112 produces a second pressure gradient which draws a flow of a second fluid 123 in the second direction 122 which is opposite the first axial direction 108. As shown in FIG. 1, the second direction 122 points from the proximal end 101 of the elongate catheter 105 toward the distal end 103 of the elongate catheter 105. In some implementations, the heart pump 100 can be used in the right heart of a patient in which case blood is pumped from the patient's inferior vena cava or right atrium, through the right ventricle into the pulmonary artery (for example, FIGS. 3 and 8). In such implementations, the first fluid 109 flows in a first axial direction 108 which may be substantially the same as the second direction 122 (not shown). In either implementation, the flow of the second fluid 123 in the second direction 122 can prevent the first fluid 109 from flowing into the bore 120. The flow of the second fluid 123 can also lubricate or cool the drive shaft 110 to prevent overheating which could cause blood coagulation, blood cell damage, seizing of the heart pump, and resulting danger to a patient. In sum, the rotation of the drive shaft 110 and the rotor 104 induces a first fluid flow 109 in the first axial direction 108 and a flow of the second fluid 123 in the second direction 122. Since the combination of the impeller blade 106 and the pump elements 112 allows the first and second flows to be induced by the same rotation, the rotor 104 can eliminate the need for a separate, dedicated pump for inducing the second fluid flow.

Figure 2:
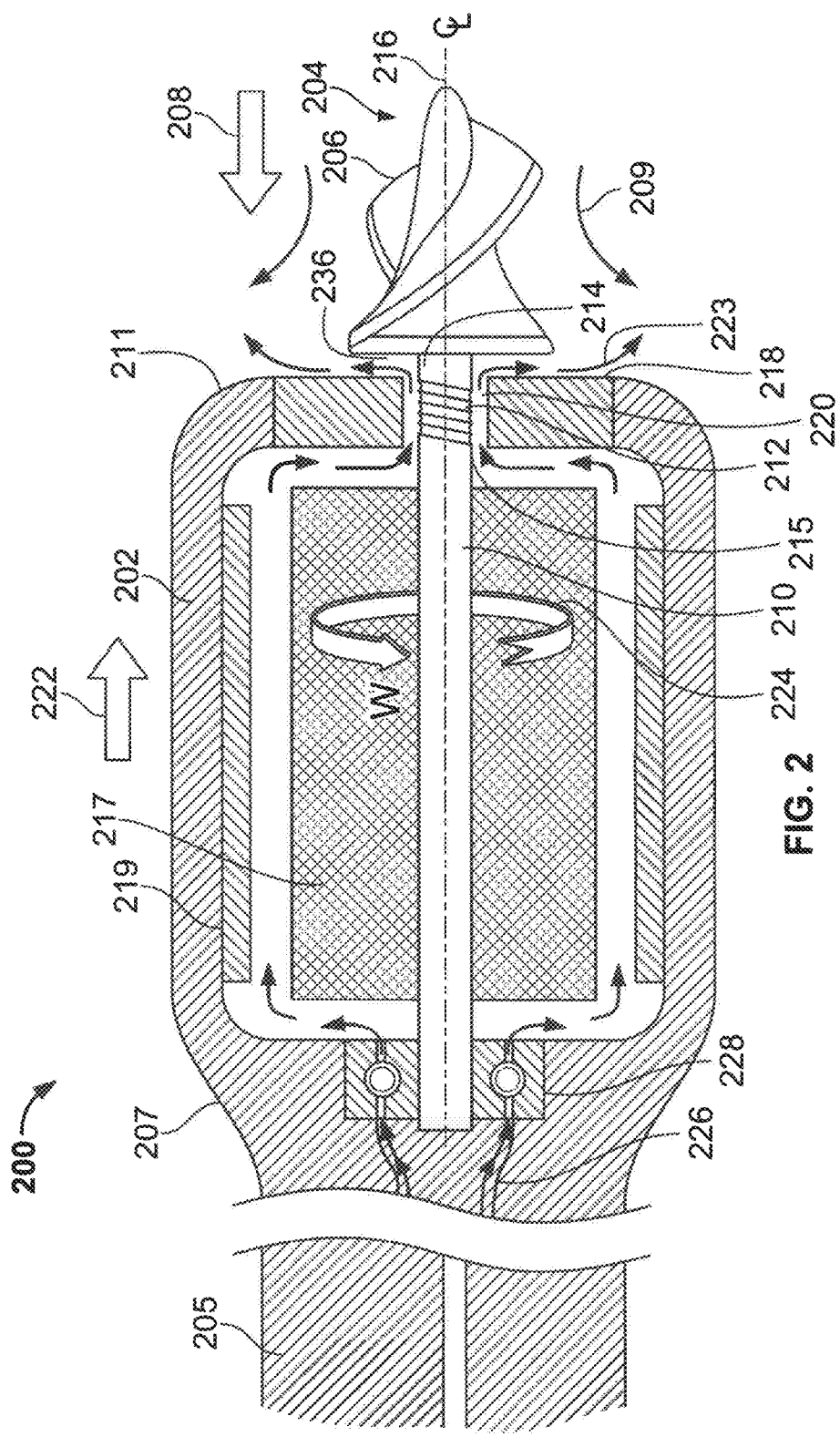
FIG. 2 shows an illustrative lateral section view of a left-heart pump having pump elements on the rotor drive shaft.

FIG. 2 shows an illustrative lateral section view of a heart pump 200 for use in the left-heart, the heart pump 200 having pump element 212 on a rotor drive shaft 210. The heart pump 200 includes an elongate catheter 205, a motor housing 202 having a proximal end 207 and a distal end 211, a drive shaft 210, a pump element 212, a motor rotor 217, a motor stator 219, a pump rotor 204, a proximal bearing 228, a distal bearing 218, and a fluid supply line 226. The pump rotor 204 includes an impeller blade 206 and is coupled to or integrally formed with the drive shaft 210. The drive shaft 210 has a longitudinal axis 216 about which it rotates in a direction 224. The drive shaft 210 includes an outer surface 214 on which a pump element 212 is formed. The drive shaft 210 is coupled to the motor rotor 217 and is rotatably coupled to the proximal and distal bearings 228 and 218. As shown, the distal bearing 218 is a sleeve bearing having a bore 220 through which the drive shaft 210 extends. The drive shaft 210 is radially spaced from the bore 220 of the distal bearing 218 by a bearing gap 215. The bearing gap 215 between the drive shaft 210 and the distal bearing 218 may be 5 microns or less. In some implementations, the bearing gap 215 may be 2 µm, 2.5 µm, 3 µm, 3.5 µm, 4 µm, 4.5 µm, 5 µm, 6 µm, or any suitable size. While in a preferred embodiment the proximal bearing 228 is a ball bearing and the distal bearing 218 is a sleeve bearing, any suitable bearing may be used for the proximal and/or distal bearings, including but not limited to ball bearings, sleeve bearings, journal bearings, hydrostatic bearings, roller bearings, and magnetic bearings.

The magnetic interaction between the motor stator 219 and motor rotor 217 rotates the drive shaft 210 in the direction 224 about the longitudinal axis 216. The motor stator 219 may be an electromagnetic coil, which may be a primary source of heat within the pump 200 due to resistive heating. In some implementations, the pump 200 is driven by a drive cable attached to an external motor. The rotation of the drive shaft 210 causes rotation of the impeller blade 206 which induces a flow of a first fluid 209 (e.g., blood) in a first direction 208 from the distal end 211 of the motor housing 202 toward the proximal end 207 of the motor housing 202. The rotation of the drive shaft 210 also induces a flow of a second fluid 223 from an external source (not shown) in a second direction 222 from the proximal end 207 of the motor housing 202 toward the distal end 211 of the motor housing 202. The flow of the second fluid 223 may flow from the external source (not shown) through the elongate catheter 205 and into the pump 200 at the proximal bearings 228. The second fluid 223 may be purge fluid, lubricant, coolant, medicine, or any suitable hemocompatible fluid. For example, the second fluid 223 may be saline, Ringer's solution, glucose solution, heparin or any other suitable fluid. In some implementations, a highly viscous purge fluid, such as a glucose solution, is used to lubricate the proximal bearings 228. In certain implementations, pharmacological agents are used as a purge fluid to purge the pump of blood or to perform a medical purpose. For example, the purge fluid may be chosen as heparin to prevent blood clotting. The flow of the first fluid 209 in the first axial direction 208 is generally opposite to the flow of second fluid 223 in the second direction 222. The flow of the second fluid 223 is tied to and depends on the rotation of the drive shaft 210.

The second fluid 223 flows to the distal end of the elongate catheter 205 from an external source through a fluid supply line 226. The second fluid 223 travels through the fluid supply line 226, past the proximal bearing 228 and into the motor housing 202. As the second fluid 223 flows past the proximal bearing 228 it may function to cool or lubricate the bearing. The rotation of the pump element 212 on the surface 214 of the drive shaft 210 generates a pressure gradient in the second fluid 223 at the bearing gap 215, thereby causing the second fluid 223 to flow through the bore 220 of the distal bearing 218 in the second direction 222. The second fluid 223 may further cool the motor stator 219 as it flows through the pump to the bearing gap 215. The second fluid 223 then exits the motor housing 202 at a fluid outlet 236. The second fluid 223 enters the patient's blood stream, where heat from the bearings or motor stator may be safely dissipated. The outflow of the second fluid 223 from the fluid outlet 236 can prevent the first fluid 209 (e.g., blood) from entering the fluid outlet 236. In cases where the first fluid is blood, this prevents the blood from entering the bore 220 and clogging the pump 200. Preventing blood from entering the bore 220 can also preserve the longevity of the heart pump 200. Thus, the heart pump 200 may be used for long-term implantation in a patient (e.g., >1 hr, >3 hr, >6 hr, >12 hr, >24 hr, >2 days, >10 days, >20 days, >45 days, >60 days, or any suitable duration). In some implementations, the flow of the second fluid 223 exits the pump and meets the flow of the first fluid 209 at a shallow angle to avoid stagnation and clot formation that may occur if the fluid flows meet head-on.

The rotor 204 and impeller blade 206 may be considered a first or primary pump element and the pump element 212 on the drive shaft 210 which induces the second fluid flow 223 of hemocompatible fluid may be considered a secondary pump element. Pumping the second fluid 223 and the blood by the same motor allows the pump 200 to be easily operated by a healthcare professional since only a single console (not shown) and pump is required. Elimination of the purge system's dedicated pump additionally reduces the space occupied by the controller for the pump system in a healthcare environment, allowing the pump to be used in smaller spaces, such as an operating room, catheterization lab or during emergency transport. The occurrence of user error causing malfunction of the purge pump can also be further limited by the use of a single motor and console to control the pumping of the second fluid and blood. Further, if the pump is configured as a fully implantable pump for long-term use, pumping the second fluid and blood by the same motor requires less external machinery or hardware for operation allowing for additional patient mobility.

In some implementations, the flow rate of the second fluid 223 in the second direction 222 is about 2-30 cc/hr. In some implementations, the flow rate of the second fluid 223 in the second direction 222 is 1.5 cc/hr, 1.75 cc/hr, 2 cc/hr, 2.25 cc/hr, 2.5 cc/hr, 5 cc/hr, 10 cc/hr, 15 cc/hr, 20 cc/hr, 25 cc/hr, 30 cc/hr, 35 cc/hr, or any other suitable flow rate. In some implementations, the flow rate of the first fluid in the first direction 208 is about 2-5 liters per minute. In some implementations, the flow rate of the blood in the first axial direction 208 is about 1 lpm, 1.5 lpm, 2 lpm, 2.5, lpm, 3 lpm, 3.5 lpm, 4 lpm, 4.5 lpm, 5 lpm, 5.5 lpm, 6 lpm, 6.5 lpm, 7 lpm, or any other suitable flow rate. In some implementations, the ratio of the flow rate of the second fluid 223 in the second direction 222 to the flow rate of the first fluid 109 in the first direction 208 is about 0.001-0.03%. In implementations in which the second fluid 223 is a hemocompatible fluid, there may be a maximum amount of hemocompatible fluid which may be discharged into a patient. The amount of hemocompatible fluid discharged into the patient may be controlled by limiting the flow rate of the second fluid. In implementations in which the first fluid is blood, the flow rate must be sufficiently high to provide circulatory support to a patient with a diseased heart to achieve normal levels of blood flow. In such cases, the required blood flow rate to be provided to the patient may be about 5-6 lpm. The flow rate of the second fluid 223 must additionally by sufficient to prevent ingress of the first fluid into the pump at the flow rate of the first fluid. In some implementations, the ratio of the flow rate of the second fluid 223 in the second direction 222 to the flow rate of the first fluid in the first direction 208 is about 0.0008%, 0.001%, 0.002%, 0.005%, 0.007%, 0.01%, 0.02%, 0.03%, 0.04%, or any other suitable ratio.

In some implementations, the heart pump 200 includes safety features in a controller (not shown) which prevent gas (e.g., air) from entering the fluid supply line 226. Disconnects or breaks in the fluid supply line 226 may result in the introduction of air to the line. By monitoring for drops in motor current indicating air in the line, the controller may alert a patient or health care professional before air moves through the fluid supply line 226.

Figure 3:
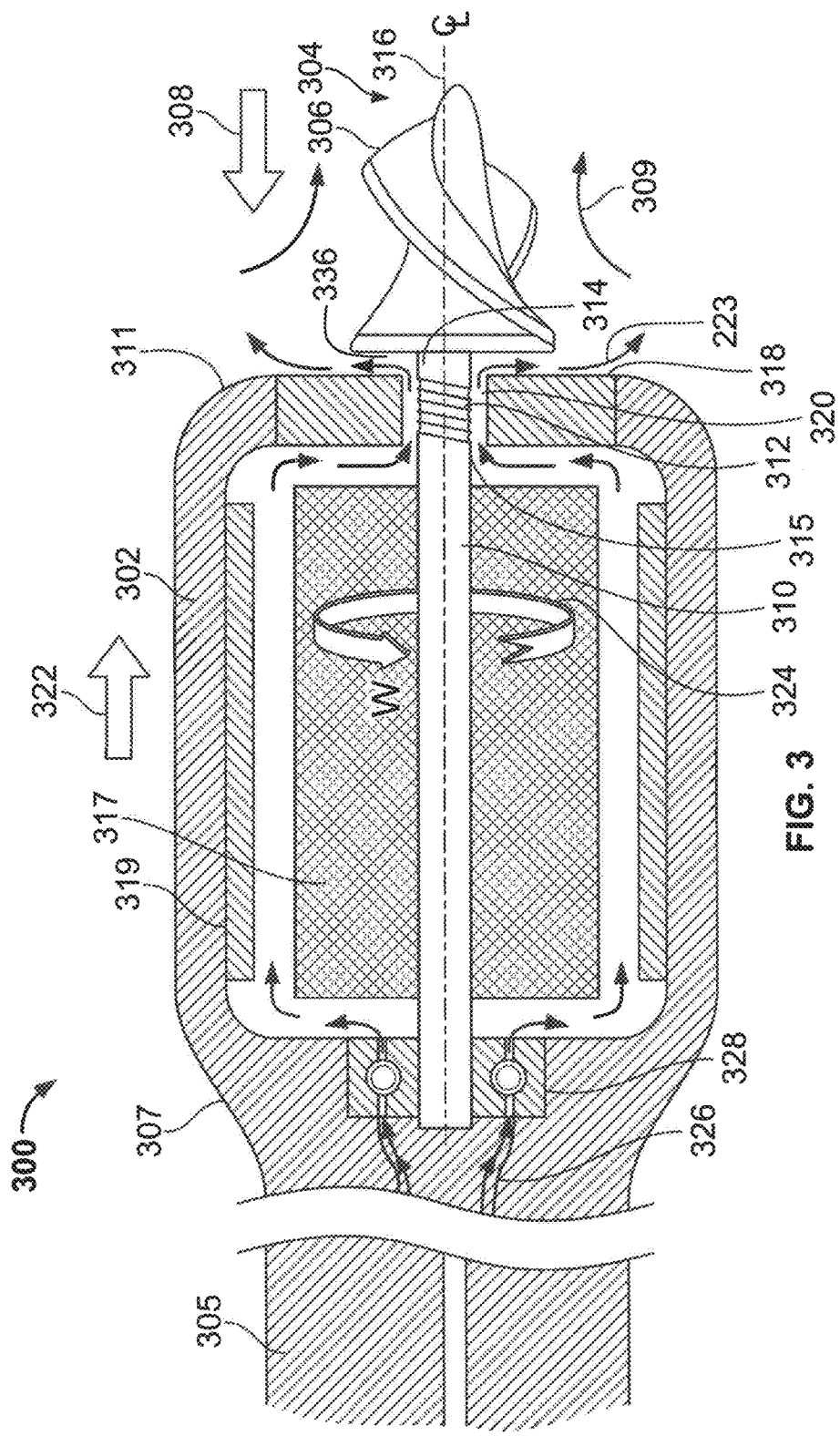
FIG. 3 shows an illustrative lateral section view of a right-heart pump having pump elements on the rotor drive shaft.

FIG. 3 shows an illustrative lateral section view of a heart pump 300 for use in the right heart, the heart pump 300 having pump elements 312 on a rotor drive shaft 310. The heart pump 300 includes an elongate catheter 305, a motor housing 302 having a proximal end 307 and a distal end 311, a drive shaft 310, a pump element 312, a motor rotor 317, a motor stator 319, a pump rotor 304, a proximal bearing 328, a distal bearing 318, and a fluid supply line 326. The pump rotor 304 includes an impeller blade 306 and is coupled to or integrally formed with the drive shaft 310. The drive shaft 310 has a longitudinal axis 316 about which it rotates in a direction 324. The drive shaft 310 includes an outer surface 314 on which a pump element 312 is formed. The drive shaft 310 is coupled to the motor rotor 317 and is rotatably coupled to the proximal and distal bearings 328 and 318. As shown, the distal bearing 318 is a sleeve bearing having a bore 320 through which the drive shaft 310 extends. The drive shaft 310 is radially spaced from the bore 320 of the distal bearing 318 by a bearing gap 315.

The heart pump 300 may be similar to a heart pump for use in the left heart (e.g., heart pump 200), but with a reversed orientation of the pump rotor 304. The pump rotor 304 induces a flow of a first fluid 309 (e.g., blood) in a first direction 308 from the proximal end 307 of the motor housing 302 toward the distal end 311 of the motor housing 302. Due to placement of the secondary pump element (pump element 312) on the drive shaft 310, the rotation of the drive shaft 310 also simultaneously induces a flow of a second fluid 323 from an external source (not shown) in a second direction 322 from the proximal end 307 of the motor housing 302 toward the distal end 311 of the motor housing 302. In blood pumps for use in the right heart, the first direction 308 and the second direction 322 are substantially the same direction. The flow of the second fluid 323 may flow from the external source (not shown) through the catheter 305 and into the pump 300 at the proximal bearings 328. The flow of the second fluid 323 is tied to and depends on the rotation of the drive shaft 310.

Figure 4:
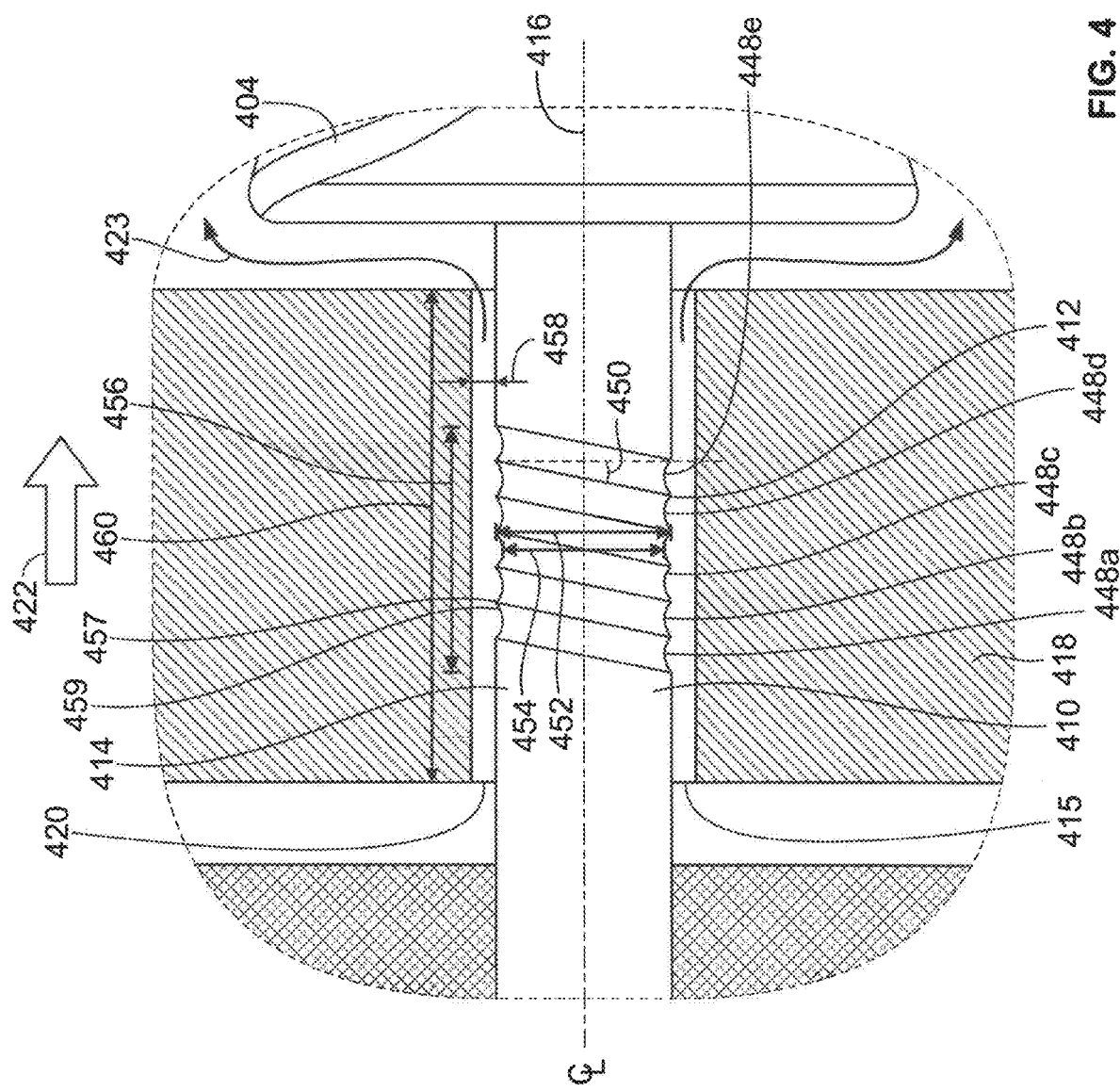
FIG. 4 shows a detailed section view of a pump element formed as a groove on a rotor drive shaft.

FIG. 4 shows a detailed section view of a pump element 412 that can be used in the blood pump of FIG. 2 or FIG. 3. The pump element 412 is formed as a groove 448 on the surface 414 of the drive shaft 410. The groove 448 forming the pump element 412 is formed at an angle with respect to the longitudinal axis 416 of the drive shaft 410. The pump element 412 may be formed at an angle of about 5.degree., 10.degree., 15.degree., 20.degree., 25.degree., 30.degree., or any other suitable angle relative to a longitudinal axis of the drive shaft 410. The groove 448 may be formed as a continuous helix having turns 448a, 448b, 448c, 448d and 448e. The helical groove 448 may include 3, 5, 7, 10, 12 turns or any other suitable number of turns around the drive shaft 410. The continuous helix may have a pitch angle 450 of about 5.degree., 10.degree., 15.degree., 20.degree., 25.degree., 30.degree., or any other suitable pitch angle. The pitch angle 450 of the helix 448 may be chosen to induce a screw motion of the pump element 412 during rotation of the drive shaft 410 to develop a pressure gradient. In some implementations, the pump element 412 acts as an impeller in developing the pressure gradient to transport a purge fluid through the stator bore 420 and out of the bearing gap 415. In certain implementations, the pump element 412 acts as a positive displacement pump by isolating the purge fluid as it is conveyed through the bearing gap 415 by the rotation of the pump element 412 on the drive shaft 410. In either implementation, the second fluid 423 may be induced to flow in a direction 422 and the flow of the second fluid 423 may be through the bearing gap 415 and out of the pump. The drive shaft 410 at the groove 448 may have a maximum diameter 452 at the peak 457 of the groove 448 of about 0.1 mm, 0.25 mm, 0.5 mm, 0.75 mm, 1 mm, 1.5 mm, 2 mm, or any other suitable diameter. The drive shaft 410 at the groove 448 may have a minimum diameter 454 at the trough 459 of the groove 448 measuring about 0.1 mm, 0.25 mm, 0.5 mm, 0.75 mm, 1 mm, 1.5 mm or any other suitable diameter. The depth of the groove 448 from trough 459 to peak 457 may be about 0.5 µm, 0.75 µm, 1 µm, 1.5 µm, 2 µm, 2.5 µm, 3 µm, or any other suitable depth.

The groove 448 may extend over the surface 414 of the drive shaft 410 along the length 460 of the bearing gap 415. The length 460 of the bearing gap 415 may be about 0.25 mm, 0.5 mm, 0.75 mm, 1 mm, 1.5 mm, 2 mm, 2.5 mm, 3 mm, 5 mm, or any other suitable length. Alternatively, the groove 448 may extend over only a portion of the surface 414 of the drive shaft 410. The grooves 448 may cover a length 456 of about 50 µm, 75 µm, 100 µm, 250 µm, 500 µm, 1000 µm, 2000 µm, or any other suitable length. The bearing gap 415 may have a width 458 of 2 µm, 2.5 µm, 3 µm, 3.5 µm, 4 µm, 4.5 µm, 5 µm, 6 µm, or any other suitable width. In some implementations, the groove trough 459 is smooth to avoid stress concentrations which may initiate formation of cracks. In some implementations, the pitch angle 450 of the groove 448 and/or the depth of the groove 448 from the trough 459 to the peak 457 is manufactured to fit a specific width 458 of the bearing gap 415. A narrow width 458 of the bearing gap 415 reduces retrograde flow that may otherwise counteract the flow induced by the pump element 412.

In some implementations, the pump elements 412 are formed by etching, centerless grinding, lathing, precision milling or by sputter coating. The pump element 412 may be machined on the drive shaft 410 by these or other processes such that the pump has tight tolerances on the details of the groove 448. In some implementations, the pump element 412 is formed as a series of distinct elements or non-continuous grooves rather than as a continuous helical groove 448 around the drive shaft 410. Forming the pump element 412 by a material removal process may result in a pump element with tighter tolerances than forming a pump element 412 as a protrusion on the drive shaft 410. Further, the formation of a pump element 412 as a groove, rather than as a protrusion, reduces risk of damage or wear to the pump element 412 or bearing 418 if the drive shaft 410 experiences eccentricities during rotation causing the pump element 412 to contact the bearing 418.

Figure 5:
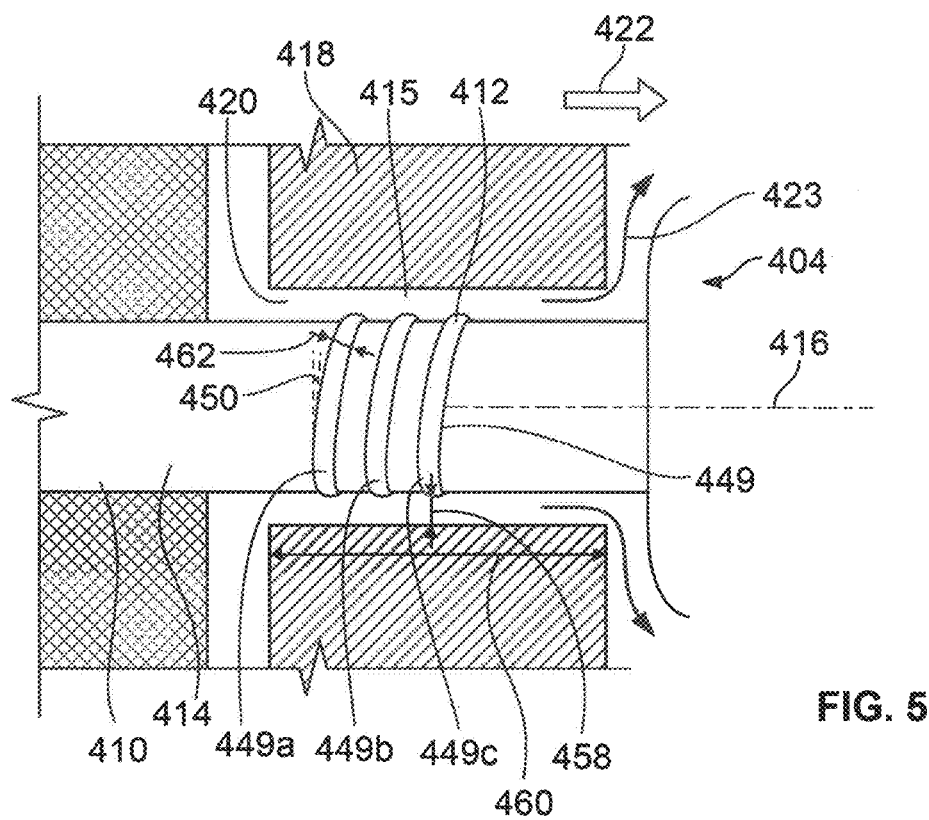
FIG. 5 shows a detailed section view of a pump element formed as a protrusion on a rotor drive shaft.

FIG. 5 shows a detailed section view of a pump element 412 formed as a protrusion on a rotor drive shaft 410 of a blood pump such as blood pump 200 in FIG. 2 or blood pump 300 in FIG. 3. The pump element 412 protrudes from the surface 414 of the drive shaft 410 into the bearing gap 415. The rotation of the drive shaft 410 rotates the pump element 412 in the bearing gap 415, inducing a flow of a second liquid 423 through the bearing gap 415. In some implementations, the rotation of the pump element 412 acts as an impeller, creating a pressure gradient to transport a purge fluid through the bearing gap 415. In other implementations, the protruding pump element 412 acts as a positive displacement pump by isolating the purge fluid as it is conveyed through the bearing gap 415. The pump element 412 is formed as a continuous helix 449 protruding from the surface 414 of the drive shaft 410. The helical pump element 412 may have an associated pitch angle 450 and a number of turns 449a-c around the drive shaft 410. The pump element 412 may be formed on the surface 414 of the drive shaft 410 along the length 460 of the bearing gap 415 or over a portion of the length 460 of the bearing gap 415. The helical protrusion 449 has a height 462 from the surface 414 of the drive shaft 410. The helical protrusion 449 may have a height 462 of about 100 micron, 200 micron, 300 micron, 400 micron or any other suitable height 462. The height 462 of the helical protrusion 449 is smaller than the width 458 of the bearing gap 415 to prevent the pump element 412 from contacting the interior of the bearing 418. The pump element 412 may be formed with an angle with respect to a longitudinal axis 416 of the drive shaft 410. In some implementations, the pump element 412 can be formed as multiple distinct unconnected protrusions on the drive shaft 410 rather than as a continuous helical protrusion. The pump element 412 may be used in pumps intended for use in the left heart (e.g., pump 200 of FIG. 2) or in pumps intended for use in the right heart (e.g., pump 300 of FIG. 3).

Figure 6:
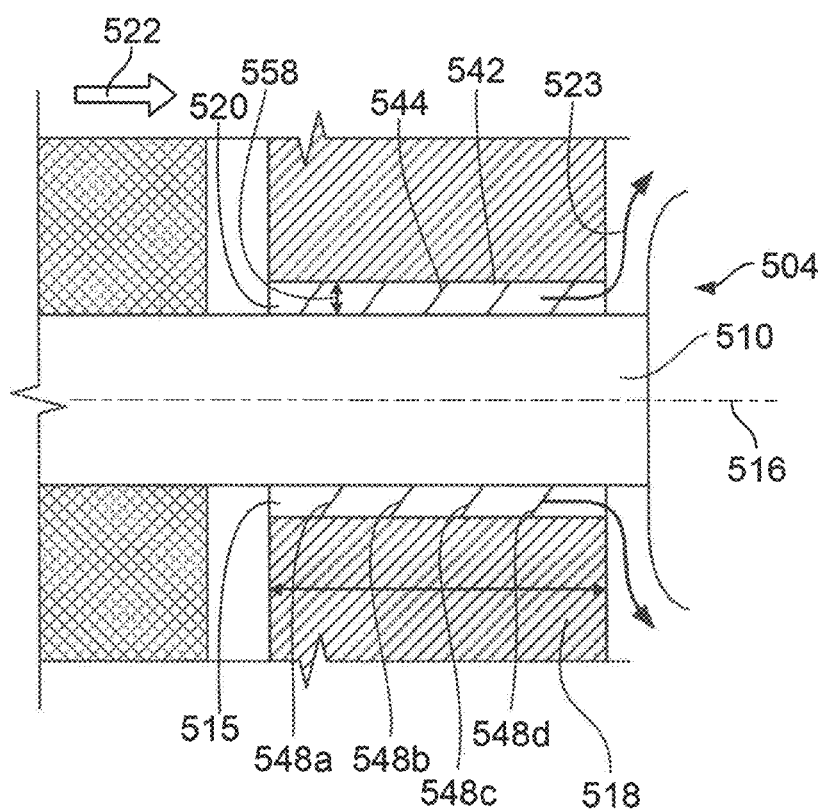
FIG. 6 shows a detailed section view of a pump element on a bearing wall.

FIG. 6 shows a detailed section view of a pump element 544 on a bearing wall 542 of a blood pump such as blood pump 200 in FIG. 2 or blood pump 300 in FIG. 3. The drive shaft 510 extends through the distal bearing 518 at the bore 520. A bearing gap 515 is formed between the drive shaft 510 and the distal bearing 518, through which fluid may flow. The distal bearing 518 includes a pump element 544 formed in an interior bearing wall 542 in the bore 520 of the distal bearing 518. As the drive shaft 510 rotates about a longitudinal axis 516, the pump element 544 on the bearing wall 542 produces a pressure gradient in the fluid when the pump element 544 is rotated relative to the bearing wall 542. This induces a second flow of fluid 523 through the bearing gap 515, in a similar manner to the pressurization of fluid in implementations in which the pump element 412 is formed on the drive shaft 410, such as in FIG. 5. The pump element 544 in the bearing wall 542 is formed as a continuous helix in the bearing wall 542. The helical pump element 544 has a number of turns 548a-d about the interior bearing wall 542. The helical pump element may have 3 turns, 5 turns, 10 turns, 15 turns, 25 turns, 50 turns or any suitable number of turns. The pump element 544 may, for example, be formed by tapping shallow screw threading into the bore 520 of the distal bearing 518. In some implementations, the pump element 544 is formed as a series of non-continuous grooves in the bearing wall 542. Forming the pump element 544 in the bearing wall 542 requires no machining of the drive shaft 510 and further may lessen the risk of fatigue failure as the bore 520 may be under less stress than the drive shaft 510.

Figure 7:
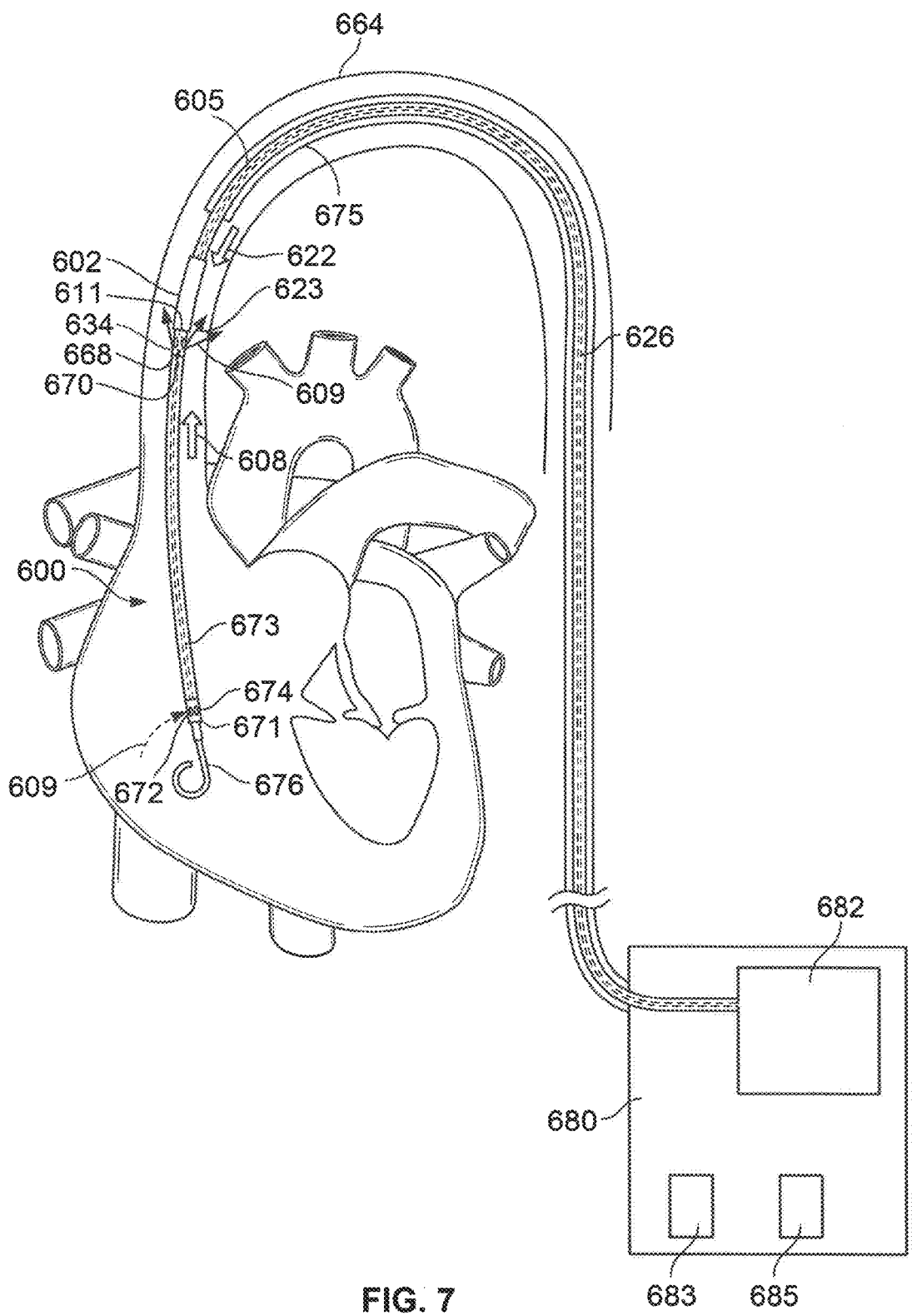
FIG. 7 shows a percutaneous left-heart pump inserted into a blood vessel of a patient.

FIG. 7 shows a percutaneous left-heart pump 600 inserted into a blood vessel of a patient. The pump 600 includes an elongate catheter body 605, a motor housing 602 and a drive shaft in which a pump element is formed. The pump 600 includes a pump housing 634, and a motor housing 602 coupled to a cannula 673 at a distal end 611 of the motor housing 602. An impeller blade (e.g., 206 in FIG. 2) on the drive shaft (e.g., 210 in FIG. 2) may be rotated within a pump housing 634 to induce a flow of blood into the cannula 673 at a suction head 674. The suction head 674 provides a blood inlet 672 at the distal end portion 671 of the cannula 673. The flow 609 of blood passes through the cannula 673 in a first direction 608 and exits the cannula 673 at one or more outlet openings 670 at the proximal end portion 668 of the cannula 673.

The rotation of the drive shaft within the pump housing 634 may also rotate a pump element (e.g., 212 in FIG. 2) within a bearing gap (e.g., 215 in FIG. 2). A hemocompatible fluid may be delivered through the elongate catheter 605 through the motor housing 602 to a proximal end portion 668 of the cannula 673 where the fluid is pressurized by the rotation of a pump element. The flow of hemocompatible fluid has a second direction 622 through the bearing gap of the pump. The pressurized fluid may prevent blood from entering the motor housing 602 to ensure continuous operation of the heart pump 600. The rotation of the drive shaft rotates the impeller blade inducing the flow of blood in the first direction 608 and also rotates the pump element within the bearing gap to produce a flow of hemocompatible fluid in a second direction 622 generally opposite the first. The rotation of the drive shaft induces both flows of fluid, such that the hemocompatible fluid flow of the pump 600 is said to be a "passive purge system," in that the flow of hemocompatible fluid is produced by the same mechanism as the flow of blood. In some implementations, the blood flow in the first direction surrounds the hemocompatible fluid flow in the second direction. When the hemocompatible fluid exits the bearing gap it may meet the flow of blood at a shallow angle preventing stagnation and coagulation of the blood which may occur if the two flows met head-on. The hemocompatible fluid prevents ingress of blood into the bearing gap. After exiting the bearing gap, the hemocompatible fluid may follow flow direction 623 and become entrained in the flow of blood and flows into the aorta with the blood.

The heart pump 600 is inserted into a vessel of the patient through a sheath 675. In some implementations no sheath is used. In other implementations, the pump is inserted using a guidewire. The elongate catheter 605 houses the fluid supply line 626 and may also house drive cables. The fluid supply line 626 supplies a hemocompatible fluid to the pump from a fluid reservoir 682. The fluid reservoir 682 may be contained in a control unit 680 which also includes controls 683 for the pump 600, including, for example, controls to power the motor or control the motor speed. The control unit 680 may also include controls 685 for the fluid supply. In some implementations, the control unit 680 includes safety features to prevent air from entering the fluid supply line 626. The control unit 680 may include circuitry for monitoring the motor current for drops in current indicating air in the line. The control unit 680 may include warning sounds, lights or indicators to alert an operator of disconnects or breaks in the fluid supply line 626 which may result in the introduction of air to the line.

The hemocompatible fluid may be flowed through the pump to prevent ingress of blood cells into the pump at the bearing gap. Alternatively, or additionally, the hemocompatible fluid may function as a lubricant for proximal or distal bearings of the pump (not shown) or as a coolant to dissipate heat produced by electromagnetic motor coils forming the motor stator (e.g., 217 in FIG. 2). The hemocompatible fluid may be purge fluid, lubricant, coolant, medicine, or any suitable hemocompatible fluid. For example, the hemocompatible fluid may be saline, Ringer's solution, glucose solution, heparin or any other suitable fluid. In some implementations, a highly viscous purge fluid, such as a glucose solution, is used to lubricate bearings internal to the pump 600. In other implementations, pharmacological agents are used as a purge fluid to purge the pump of blood as well as perform a medical purpose. For example, the purge fluid may be chosen as heparin to prevent blood clotting. The purge fluid flows through the fluid supply line 626, through the bearing gap, and flows out of the pump 600 at the outlet openings 670 near the proximal end portion 668 of the cannula 673. The purge fluid is safely dispersed into the blood stream of the patient.

The pump housing 634 may enclose the pump rotor (e.g., 204 in FIG. 2) and internal bearings. The pump housing 634 may be sized for percutaneous insertion into a vessel of a patient. The pump housing 634 may have an outer diameter of about 4 mm and may be about 15 mm in length. The pump may be percutaneously inserted into the femoral artery near the groin and advanced through the vasculature to the heart. Blood may flow in the first axial direction 608 when blood is pumped from a patient's left ventricle into the patient's aorta to increase cardiac output. In some implementations, the pump may be advanced through the vasculature and over the aortic arch 664. Although the pump is shown in the left ventricle, the pump may alternatively be placed in the right heart, such that the blood is pumped from the patient's inferior vena cava or right atrium, through the right ventricle into the pulmonary artery.

A flexible projection 676 may also be included at a distal end portion 671 of the cannula 673, distal to the suction head 674, in order to position the heart pump 600 optimally in a vessel or chamber of the heart. The flexible projection 676 may prevent the suction head 674 from approaching the wall of the vessel where it may become stuck due to suction. The flexible projection 676 may extend the pump 600 mechanically, but not hydraulically, as the flexible projection 676 may be non-sucking. In some implementations, the flexible projection may be formed as a pigtail. In other implementations, the flexible projection 676 may be straight or curved. In some implementations, the flexible projection 676 may be round or formed as a ball. The flexible projection 676 maintains the distance of the suction head 674 from a wall of the vessel in order to ensure efficiency of the heart pump 600. In some embodiments, the pump need not include a flexible projection.

Figure 8:
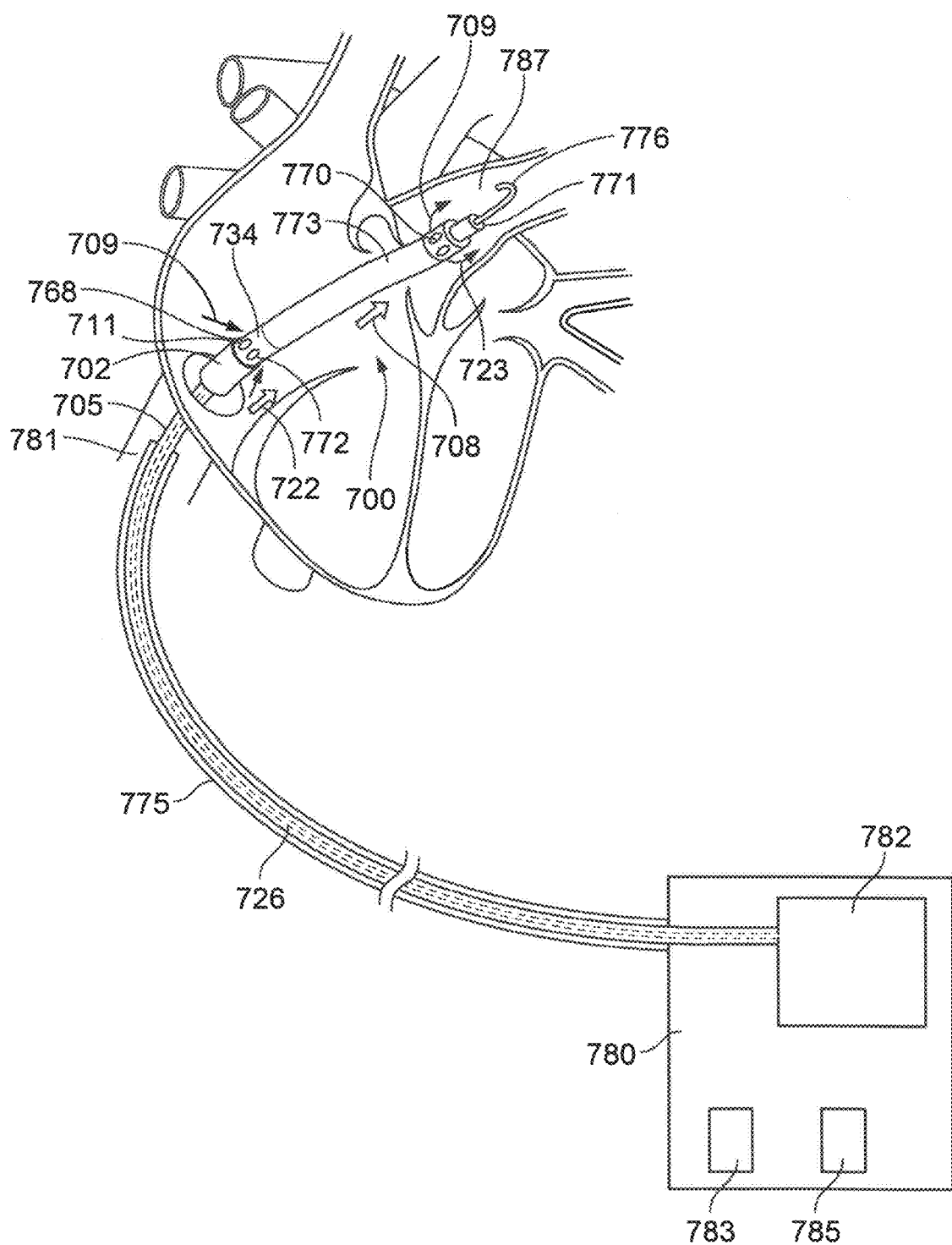
FIG. 8 shows a percutaneous right-heart pump inserted into a blood vessel of a patient.

FIG. 8 shows a percutaneous right-heart pump 700 inserted into a blood vessel of a patient. The pump 700 comprises elements similar to those of the pump 600 of FIG. 7. The pump 700 includes a pump housing 734, and a motor housing 702 coupled to a cannula 773 at a distal end 711 of the motor housing 702. An impeller blade (e.g., 306 in FIG. 3) disposed on the drive shaft (e.g., 310 in FIG. 3) may be rotated within the pump housing 734 to induce a flow of blood into the cannula 773 at a blood inlet 772 at the proximal end portion 768 of the cannula 773. A blood outlet 770 is provided at the distal end portion 771 of the cannula 773. A flow 709 of blood may enter into blood inlets 772 at a proximal end portion 768 of the cannula 773 in a first direction 708 and the flow of blood 709 may exit the cannula 773 at one or more outlet openings 770 at the distal end portion 771 of the cannula 773.

The rotation of the drive shaft within the pump housing 734 may also rotate a pump element (e.g., 312 in FIG. 3) within a bearing gap (e.g., 315 in FIG. 3). A hemocompatible fluid may be delivered through the elongate catheter 705 through the motor housing 702 to a proximal end portion 768 of the cannula 773 where the fluid is pressurized by the rotation of a pump element. The flow of hemocompatible fluid has a second direction 722 through the bearing gap of the pump. The pressurized fluid may prevent blood from entering the motor housing 702 to ensure continuous operation of the heart pump 700. The rotation of the drive shaft rotates the impeller blade inducing the flow of blood in the first direction 708 and also rotates the pump element within the bearing gap to produce a flow of hemocompatible fluid in a second direction 722 which is the same as the first direction 708. The rotation of the drive shaft induces both flows of fluid, such that the hemocompatible fluid flow of the pump 700 is said to be a "passive purge system," in that the flow of hemocompatible fluid is produced by the same mechanism as the flow of blood. The hemocompatible fluid prevents ingress of blood into the bearing gap. After exiting the bearing gap, the hemocompatible fluid follows the flow direction 723 and may become entrained in the flow of blood into the pulmonary artery 787.

In a similar manner as the heart pump 600 of FIG. 7, the heart pump 700 is inserted into a vessel of the patient through a sheath 775. In some implementations, no sheath is used. In other implementations, the pump is inserted using a guidewire. The pump 700 may be positioned such that blood enters the pump in the inferior vena cava 781 and exits the pump into the pulmonary artery 787. The elongate catheter 705 houses the fluid supply line 726 and may also house drive cables. The fluid supply line 726 supplies a hemocompatible fluid to the pump from a fluid reservoir 782. The fluid reservoir 782 may be contained in a control unit 780 which also includes controls 783 for the pump 700, including, for example, controls to power the motor or control the motor speed. The control unit 780 may also include controls 785 for the fluid supply. In some implementations, the control unit 780 includes safety features to prevent air from entering the fluid supply line 726. The control unit 780 may include circuitry for monitoring the motor current for drops in current indicating air in the line. The control unit 780 may include warning sounds, lights or indicators to alert an operator to disconnects or breaks in the fluid supply line 726 which may result in the introduction of air to the line.

The hemocompatible fluid may be flowed through the pump to prevent ingress of blood cells into the pump at the bearing gap. Alternatively, or additionally, the hemocompatible fluid may function as a lubricant for proximal or distal bearings of the pump (not shown) or as a coolant to dissipate heat produced by electromagnetic motor coils forming the motor stator (e.g., 317 in FIG. 3). The hemocompatible fluid may be purge fluid, lubricant, coolant, medicine, or any suitable hemocompatible fluid. The purge fluid flows through the fluid supply line 726, through the bearing gap, and flows out of the pump 700 at the outlet openings 770 near the distal end portion 771 of the cannula 773. The purge fluid is safely dispersed into the blood stream of the patient.

The pump housing 734 may enclose the pump rotor (e.g., 304 in FIG. 3) and internal bearings. The pump 700, and in particular the pump housing 734, may be sized for percutaneous insertion into a vessel of a patient. The pump housing 734 may have an outer diameter of about 4 mm and may be about 15 mm in length. The pump may be percutaneously inserted into the femoral artery near the groin and advanced through the vasculature to the heart. Blood may flow in the first axial direction 708 when blood is pumped from a patient's inferior vena cava 781 into the patient's pulmonary artery 787. A flexible projection 776 may also be included at a distal end portion 771 of the cannula 773, in order to position the heart pump 700 optimally in a vessel or chamber of the heart. In some embodiments, the pump need not include a flexible projection.

Figure 9:
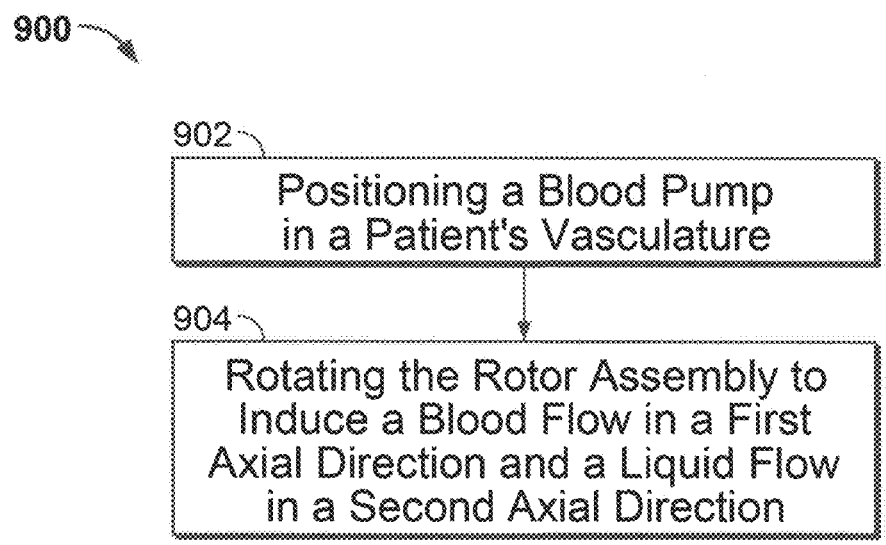
FIG. 9 shows an illustrative process for providing cardiac assistance.

FIG. 9 shows an illustrative process 900 for providing cardiac assistance. In step 902, a heart pump (e.g., heart pump 100 of FIG. 1, heart pump 200 of FIG. 2, heart pump 600 of FIG. 7, heart pump 700 of FIG. 8, or any other suitable heart pump) is positioned in a patient's vasculature. The heart pump may be configured for short-term use, such as during an emergency procedure or in conjunction with an imaging procedure. In some implementations, the heart pump may be configured for long-term use as a fully implantable heart pump. The heart pump may be used for long-term implantation in a patient (e.g., >1 hr, >3 hr, >6 hr, >12 hr, >24 hr, >2 days, >10 days, >20 days, >45 days, >60 days or any suitable duration). The heart pump may be inserted into the patient's vasculature surgically or percutaneously. In some implementations, the heart pump is advanced into position over a guidewire and/or through a sheath. The heart pump may be used in the left-heart to pump blood from a patient's left ventricle into the patient's aorta to increase cardiac output. In some implementations, the heart pump is advanced over the aortic arch. In other implementations, the heart pump is positioned in the right-heart to pump blood from the patient's inferior vena cava or right atrium, through the right ventricle into the pulmonary artery.

Once the pump has been positioned, in step 904, the pump rotor assembly is rotated to induce a first fluid flow in a first axial direction and a second fluid flow in a second direction generally opposite the first fluid flow. The pump rotor (e.g., rotor 103 in FIG. 1, rotor 204 in FIG. 2, rotor 304 in FIG. 3 or any other suitable rotor) may be rotated on a drive shaft (e.g., drive shaft 110, drive shaft 210, drive shaft 310, drive shaft 410, drive shaft 510, or any other suitable drive shaft) having a pump element (e.g., pump element 112, pump element 212, pump element 312, pump element 412, pump element 544, or any other suitable pump element). The pump element may be formed as a groove, etching or protrusion on the surface of the rotatable drive shaft, such that the rotation of the drive shaft within a bearing gap (e.g., bearing gap 215, bearing gap 315, bearing gap 415, bearing gap 515, or any other suitable bearing gap) produces a pressure gradient that draws a second fluid flow through the bearing gap. In some implementations, the pump element may be formed as a groove, etching, or protrusion on an interior wall of a distal bearing (e.g., pump element 544 of FIG. 6). In some implementations, the first fluid flow and the second fluid flow are opposite to each other at the point that the first fluid flow and second fluid flow meet. In some implementations, the first fluid flow in the first direction surrounds the second fluid flow in the second direction. In some implementations, the first liquid flow and the second liquid flow meet at a shallow angle. In some implementations, the first fluid flow and the second fluid flow are in an axial direction generally opposite each other. In some implementations, the first fluid flow and the second fluid flow are perpendicular to each other. In some implementations, the first fluid flow and the second fluid flow are skew from one another.

The first fluid may be induced to flow in the first axial direction by an impeller. The second fluid may be induced by the pump element formed on the drive shaft. In some implementations, the flow rate of the second fluid in the second direction is about 2-30 cc/hr. In some implementations, the flow rate of the second fluid in the second direction is 1.5 cc/hr, 1.75 cc/hr, 2 cc/hr, 2.25 cc/hr, 2.5 cc/hr, 5 cc/hr, 10 cc/hr, 15 cc/hr, 20 cc/hr, 25 cc/hr, 30 cc/hr, 35 cc/hr, or any other suitable flow rate. In some implementations, the flow rate of the first fluid in the first direction is about 2-5 liters per minute. In some implementations, the flow rate of the blood in the first axial direction is about 1 lpm, 1.5 lpm, 2 lpm, 2.5, lpm, 3 lpm, 3.5 lpm, 4 lpm, 4.5 lpm, 5 lpm, 5.5 lpm, 6 lpm, 6.5 lpm, 7 lpm, or any other suitable flow rate. In some implementations, the ratio of the flow rate of the second fluid in the second direction to the flow rate of the first fluid in the first direction is about 0.001-0.03%. In implementations in which the second fluid is a hemocompatible fluid, there may be a maximum amount of hemocompatible fluid which may be discharged into a patient. The amount of hemocompatible fluid discharged into the patient may be controlled by limiting the flow rate of the second fluid. In implementations in which the first fluid is blood, the flow rate must be sufficiently high to provide circulatory support to a patient with a diseased heart to achieve normal levels of blood flow. In such cases, the required blood flow rate to be provided to the patient may be about 5-6 lpm. The flow rate of the second fluid must additionally by sufficient to prevent ingress of the first fluid into the pump at the flow rate of the first fluid. In some implementations, the ratio of the flow rate of the second fluid in the second direction to the flow rate of the first fluid in the first direction is about 0.0008%, 0.001%, 0.002%, 0.005%, 0.007%, 0.01%, 0.02%, 0.03%, 0.04%, or any other suitable ratio. The flow of fluid counter to the direction of the blood flow can lubricate the bearings within the pump, purge the pump of excess heat and/or blood that has entered, and can prevent the ingress of blood cells into the heart pump.

The pump elements integrated into the drive shaft or bearing wall of the heart pump allow the pump to induce simultaneous fluid flow in different directions. By simultaneously pumping blood and a hemocompatible fluid by the same mechanism, the need for an external pressurizing pump to pump purge fluid is eliminated or reduced. Eliminating the purge fluid external pump reduces the size of an external controller of the pump in a healthcare environment and simplifies the workflow for an operator to setup and/or use the external controller. In use as a fully implantable pump for long-term implantation, the elimination of the additional pump may increase patient mobility. Furthermore, the flow of the second fluid can provide a barrier against blood ingress into sensitive regions of the pump (e.g., the bore in which the rotor shaft rotates), and/or lubricate bearings within the pump. These effects can allow the pump to be used on a long-term basis without requiring additional equipment for a purge fluid.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for providing cardiac assistance, the method comprising:
   positioning a heart pump in a patient's vasculature, wherein the heart pump comprises:
      an elongate catheter having a proximal portion and a distal portion;
      a pump rotor disposed at the distal portion of the elongate catheter, the pump rotor having an impeller blade;
      a drive shaft coupled to the pump rotor;
      a bearing disposed at the distal portion of the elongate catheter and having a bore into which the drive shaft extends; and
      a pump element formed in the drive shaft and disposed at the distal portion of the elongate catheter;
   rotating the drive shaft to induce a blood flow in a first axial direction with the impeller blade while concurrently inducing a fluid flow through the bore and into the patient's vasculature in a second axial direction with the pump element.

2. The method of claim 1, wherein a flow rate of the fluid flow induced in the second axial direction by the pump element is less than 1% of a flow rate of the blood flow induced in the first axial direction by the impeller blade.

3. The method of claim 1, wherein a flow rate of the fluid flow induced in the second axial direction by the pump element is about 0.001-0.03% of a flow rate of the blood flow induced in the first axial direction by the impeller blade.

4. The method of claim 1, wherein a flow rate of the blood flow induced in the first axial direction by the impeller blade is about 2-5 liters per minute.

5. The method of claim 1, wherein a flow rate of the fluid flow induced in the second axial direction by the pump element is about 2-30 cubic centimeters per hour.

6. The method of claim 1, wherein the second axial direction is opposite to the first axial direction.

7. The method of claim 1, wherein the second axial direction is substantially identical to the first axial direction.

8. The method of claim 1, wherein the fluid flow induced by the pump element is of a fluid drawn through a fluid supply line within the elongate catheter.

9. The method of claim 1, wherein inducing the fluid flow comprises inducing a flow of saline.

10. The method of claim 1, wherein inducing the fluid flow comprises inducing a flow of Ringer's solution.

11. The method of claim 1, wherein inducing the fluid flow comprises inducing a flow of glucose solution.

12. The method of claim 1, wherein inducing the fluid flow comprises inducing a flow of heparin.

13. The method of claim 1, wherein the heart pump further comprises a bearing gap between an inner surface of the bore and the drive shaft, the bearing gap being about 5 microns or less.

14. The method of claim 1, wherein the heart pump further comprises a bearing gap between an inner surface of the bore and the drive shaft, the bearing gap being in a range of about 5-15 microns.

15. The method of claim 1, wherein the blood flow in the first axial direction surrounds the fluid flow in the second axial direction.

16. The method of claim 1, wherein the pump element is shaped as a groove on a surface of the drive shaft.

17. The method of claim 16, wherein the groove on the surface of the drive shaft is angled with respect to a longitudinal axis of the drive shaft.

18. The method of claim 1, wherein the pump element is shaped as a protrusion on a surface of the drive shaft.

19. The method of claim 1, wherein the drive shaft is coupled to a motor.

20. The method of claim 1, wherein positioning the heart pump in the patient's vasculature comprises percutaneously implanting the heart pump into the patient's heart.

* * * * *